(12) United States Patent
Menot et al.

(10) Patent No.: US 8,298,183 B2
(45) Date of Patent: Oct. 30, 2012

(54) MEDICAL LIQUID INJECTION DEVICE

(75) Inventors: Sébastien Menot, Thoiry (FR); Niklaus Schneeberger, Höniz (CH); Frédéric Neftel, Lausanne (CH)

(73) Assignee: Debiotech S.A., Lausanne (CH)

( * ) Notice: Subject to any disclaimer, the term of this patent is extended or adjusted under 35 U.S.C. 154(b) by 358 days.

(21) Appl. No.: 12/295,014

(22) PCT Filed: Mar. 17, 2007

(86) PCT No.: PCT/IB2007/050932
§ 371 (c)(1),
(2), (4) Date: Oct. 21, 2010

(87) PCT Pub. No.: WO2007/113708
PCT Pub. Date: Oct. 11, 2007

(65) Prior Publication Data
US 2011/0054397 A1    Mar. 3, 2011

(30) Foreign Application Priority Data

Mar. 31, 2006    (EP) ..................................... 06112066

(51) Int. Cl.
*A61M 5/00*    (2006.01)
(52) U.S. Cl. ...................................................... 604/151
(58) Field of Classification Search ................... 604/110, 604/131, 151
See application file for complete search history.

(56) References Cited

U.S. PATENT DOCUMENTS

| | | | |
|---|---|---|---|
| 2,705,953 A | | 4/1955 | Potez |
| 4,360,019 A | * | 11/1982 | Portner et al. ................ 604/131 |
| 4,373,527 A | | 2/1983 | Fischell |
| 4,487,603 A | | 12/1984 | Harris |
| 4,604,090 A | * | 8/1986 | Reinicke ........................ 604/118 |
| 4,808,167 A | * | 2/1989 | Mann et al. .................... 604/151 |
| 4,850,972 A | * | 7/1989 | Schulman et al. ............. 604/151 |
| 4,874,386 A | | 10/1989 | O'Boyle |
| 5,098,409 A | | 3/1992 | Stock |
| 5,167,633 A | * | 12/1992 | Mann et al. .................... 604/141 |
| 5,176,644 A | * | 1/1993 | Srisathapat et al. .......... 604/141 |

(Continued)

FOREIGN PATENT DOCUMENTS

CN    1047368 A    11/1990

(Continued)

OTHER PUBLICATIONS

Chinese Office Action dated Oct. 2010, and its English translation.

(Continued)

*Primary Examiner* — Nicholas Lucchesi
*Assistant Examiner* — Aarti B Berdichevsky
(74) *Attorney, Agent, or Firm* — Nixon & Vanderhye P.C.

(57) ABSTRACT

Medical liquid injection device comprising the following distinct elements: a container (1), an outlet channel (14) and a pumping unit (5); said container (1) comprising a rigid wall on which said pumping unit (5) is rigidly fixed; said rigid wall furthermore including a passage (4) which forms a direct fluid connection between said pumping unit (5) and said container (1); said outlet channel (14) being directly connected to said pumping unit (5) in such a way that a fluid initially kept in said container (1) may first flow through said pumping unit (5) and then reach said outlet channel (14), said medical liquid injection device furthermore comprising an inlet (16), distinct from said outlet channel (14), and disposable elements.

34 Claims, 3 Drawing Sheets

U.S. PATENT DOCUMENTS

| | | | |
|---|---|---|---|
| 5,205,819 A * | 4/1993 | Ross et al. | 604/67 |
| 5,224,843 A | 7/1993 | Van Lintel | |
| 5,257,971 A * | 11/1993 | Lord et al. | 604/500 |
| 5,938,640 A | 8/1999 | Maget et al. | |
| 6,948,918 B2 * | 9/2005 | Hansen | 417/395 |
| 7,914,500 B2 * | 3/2011 | Gafner-Geiser et al. | 604/192 |
| 2003/0050623 A1 | 3/2003 | Lord et al. | |
| 2003/0055323 A1 * | 3/2003 | Choi | 600/316 |
| 2003/0100864 A1 | 5/2003 | Bendsen et al. | |
| 2004/0115068 A1 * | 6/2004 | Hansen et al. | 417/379 |

FOREIGN PATENT DOCUMENTS

| | | |
|---|---|---|
| EP | 0398583 | 11/1990 |
| EP | 1527792 A1 | 5/2005 |
| JP | 9-505208 | 5/1997 |
| JP | 2004-505212 | 2/2004 |
| WO | WO 85/02123 | 5/1985 |
| WO | WO 85/02123 A1 | 5/1985 |
| WO | WO 95/03078 | 2/1995 |
| WO | WO 01/90577 | 11/2001 |
| WO | WO 2005/039674 A1 | 5/2005 |
| WO | WO 2005/105182 A1 | 11/2005 |
| WO | WO 2007/077255 A2 | 7/2007 |
| WO | WO 2007/113708 A1 | 10/2007 |

OTHER PUBLICATIONS

Roche Opposition filed at EPO Oct. 19, 2010.
Sanofi Opposition filed at EPO Oct. 20, 2010.
Patent Owner's Reply to Oppositions dated Mar. 25, 2011.
International Preliminary Report on Patentability for PCT/IB2007/050932 dated Sep. 30, 2008, and Written Opinion (including a copy of the ISR that was already submitted w/IDS of Sep. 29, 2008).

* cited by examiner ion of the container from the patient. Because the container content has to remain sterile, it can be considered to refill it several times, up to the specified lifetime of the drug in such a sterile type of reservoir. After this lifetime the container and all others parts that are wetted by the drug are preferably discarded. Several other parts of the device, notably the driving electronics and user interface can be used permanently. The pumping unit according to the invention preferably consists of a permanent part and a disposable part. The disposable part contains, as mentioned above, all the elements that are wetted by the drug, i.e. the container, the pumping unit, the inlet, and the connection port for the infusion line. The parts
MEDICAL LIQUID INJECTION DEVICE

FIELD OF INVENTION

The present invention relates to medical containers for liquid substances, e.g. insulin, which are adapted to be fixed to an injection device, such as a pump, which administers the liquid substance to a patient over an extended period.

STATE OF THE ART

Administering a liquid medical substance, e.g. insulin, to a patient is usually made with a syringe pump. See for instance WO 2004/084976 or US 2003/055323.

The liquid is contained in a syringe which is has to be pre-filled before the treatment.

When the syringe is empty, a new pre-filled syringe is used.

A new pre-filled syringe may also be needed if the first syringe is partially empty, for instance when the patient wishes to have a completely full container before starting an activity or before traveling.

GENERAL DESCRIPTION OF THE INVENTION

One objective of the invention is to reduce the number of containers used during a treatment.

Another objective of the invention is to provide an easy and comfortable way to administer a liquid medical substance over a long period.

Those objectives are achieved with the medical injection device according to the invention which includes at least the following distinct elements: a container, an outlet channel and a pumping unit; said container comprising a rigid wall on which said pumping unit is rigidly fixed; said rigid wall furthermore including a passage which forms a direct fluid connection between said pumping unit and said container; said outlet channel being directly connected to said pumping unit in such a way that a fluid initially kept in said container may first flow through said pumping unit and then reach said outlet channel, said medical liquid injection device furthermore comprising an inlet, distinct from said outlet channel, which is adapted to act as refilling means. In addition, the medical injection device according to the invention comprises disposable parts.

The present invention offers in particular the following advantages:
  Avoid a waste of containers, only one is used,
  Easy and comfortable way to administer medical liquid without interruption,
  Possible to have a container of a relative small size.

The device according to the invention may advantageously be used as a drug infusion pump. In contrast to the state-of-the-art devices, i.e. syringe drives, the pumping unit according to the invention offers a permanent occlusion between the container and the patient line, thus preventing a contamination of the container from the patient. Because the container content has to remain sterile, it can be considered to refill it several times, up to the specified lifetime of the drug in such a sterile type of reservoir. After this lifetime the container and all others parts that are wetted by the drug are preferably discarded. Several other parts of the device, notably the driving electronics and user interface can be used permanently. The pumping unit according to the invention preferably consists of a permanent part and a disposable part. The disposable part contains, as mentioned above, all the elements that are wetted by the drug, i.e. the container, the pumping unit, the inlet, and the connection port for the infusion line. The parts can be connected and disconnected repeatedly. In particular the permanent part can be reused with several disposable parts.

DETAILED DESCRIPTION OF THE INVENTION

An embodiment of the invention is discussed below in a more detailed way together with the following figures.

Figure 1:
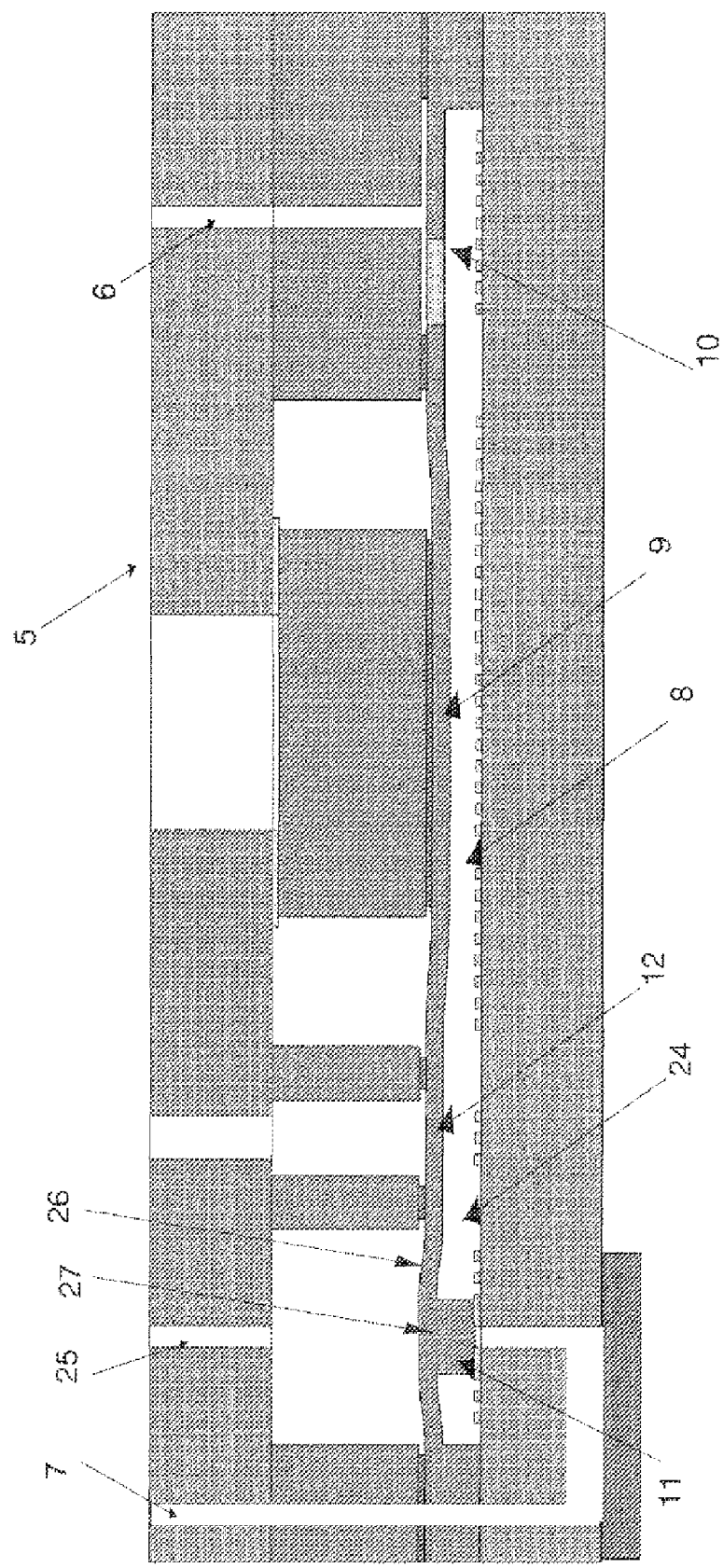
FIG. 1 is a cross-section view of a medical liquid injection device.
Figure 2:
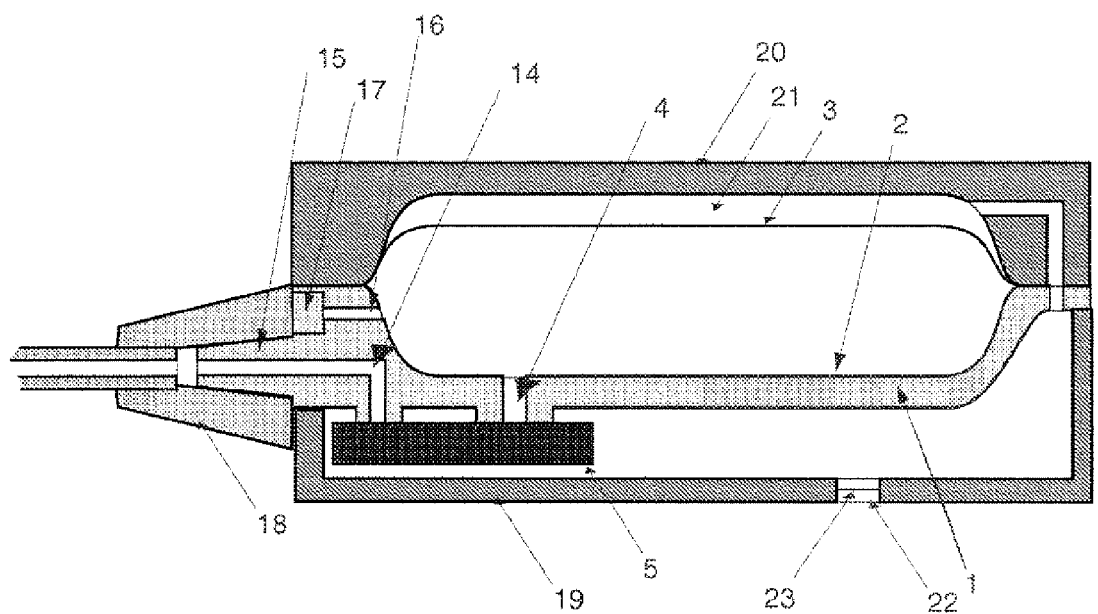
FIG. 2 is an enlarged view of the pumping unit illustrated in FIG. 1.
Figure 3:
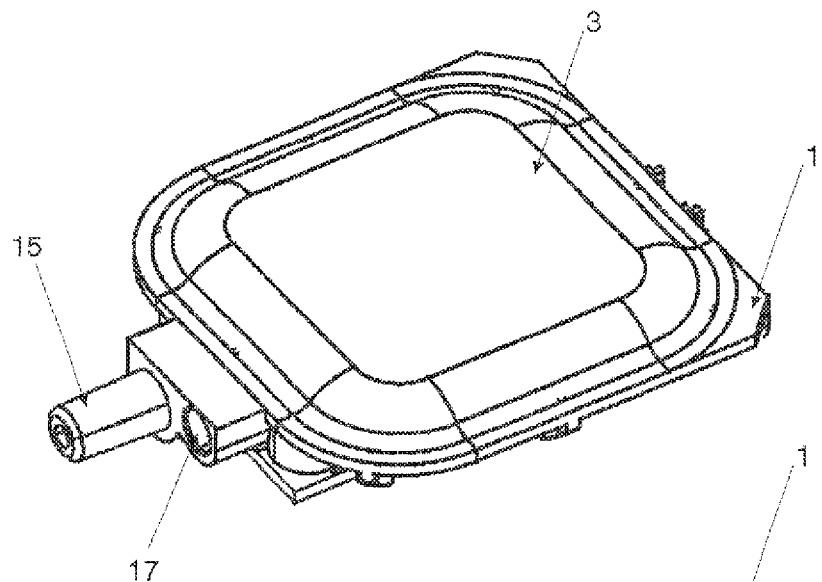
FIG. 3 is a perspective upper view of the device of FIG. 1, with a flexible membrane but without the bottom and the upper protective shells.
Figure 4:
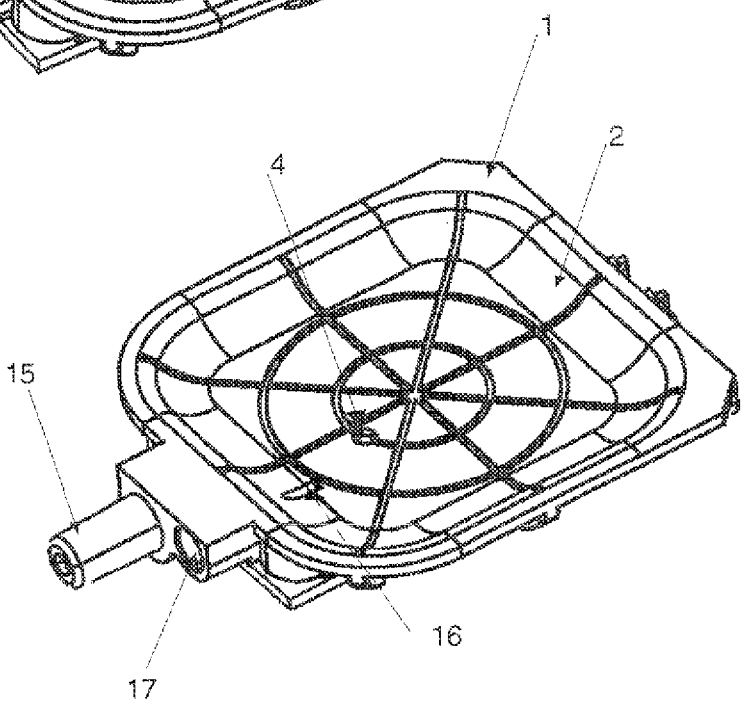
FIG. 4 is represents the same object than the object of FIG. 3 but without the flexible membrane.
Figure 5:
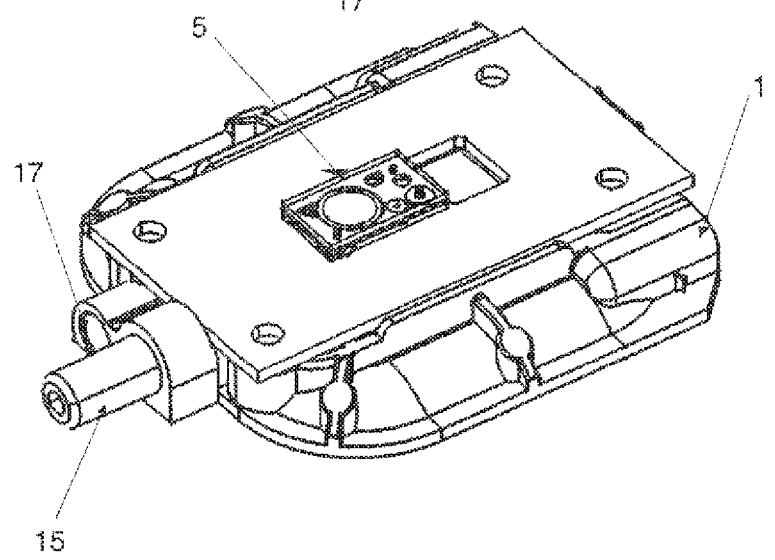
FIG. 5 is a perspective bottom view of the device of FIG. 1.

The medical liquid injection device illustrated on the figures, and more precisely its disposable part, is mainly built around one piece forming an hard shell 1. This hard shell 1 serves as structural base and fluidic interconnect between the functional elements in the disposable, and as functional element as well. It is a shell like structure presenting two major surfaces, one having a concave surface and forming thereby a cavity 2. A flexible film 3 is attached all around the periphery of this cavity 2, closing it off. They are thus forming a closed cavity, whose volume is variable because of the flexibility of the film 3. The film 3 is thermoformed to conform to the shape of the cavity 2 when it collapses into the cavity 2 such that the remaining volume is negligible.

A first passage 4 is crossing the hard shell from the cavity 2 to the opposite side, on which is mounted a microfluidic pumping unit 5. The microfluidic pumping unit 5 has an inlet 6 and an outlet port 7 on one of the two principal faces.

The fluidic connection between the pumping unit 5 and the hard shell 1 is made by aligning the first passage 4 of the hard shell 1 and the inlet port 6 of the pumping unit 5. Tightness is easily achieved with elastomeric O-rings between the two surfaces.

The microfluidic pumping unit 5 is a fabricated using micromachining techniques. It is a positive displacement pump. It features a pumping chamber 8 with an elastic membrane 9 that is cyclically compressed and decompressed by the movement of the membrane 9. Fluid flow is directed by a passive inlet 10 and a passive outlet check valve 11 connected to the pumping chamber. The pumping unit 5 also features a pressure sensor 12 monitoring the pressure inside the fluid path. Electrical lines and contacts link this sensor 12 and the actuator driving the movement of the membrane to the permanent part that contains the necessary circuits.

An outlet channel 14 in the hard shell 1 links the outlet port 7 of the pumping unit to a Luer type connector 15 for the infusion line.

A third channel 16, acting as an inlet, is crossing the hard shell 1, leading into the cavity 2 and is closed off by a septum 17 on the outside, that allows to fill and refill the container using e.g. a needle and syringe. The septum 17 is located next to the connector for the infusion line. The mating connector 18 on the infusion line is shaped in such a fashion that it covers the refilling septum while connected. This is done to prevent the users from refilling the reservoir while somebody is connected to the device.

The elements described form the principal functional structure of the disposable and are called the fluidic block.

The fluidic block is housed between two rigid shells 19, 20, mainly for mechanical protection. In particular the flexible film 3 must be protected from mechanical forces to prevent pressurizing the drug in the container. In case of excessive pressure in the container the two passive check valves in the pump might be forced open and dangerous amounts of drug could be injected into the patient. The pressure in the volume 21 between the flexible film 3 and the rigid outer shell 20 is equilibrated through a vent 22. Water ingress into this volume is prevented through the use of a hydrophobic filter membrane 23. If this vent becomes blocked dangerous overpressure on the flexible membrane 3 may occur. To prevent opening of the check valves an anti-free-flow check valve is used in the pumping unit. As shown in the drawing this valve features three ports: a fluidic inlet port 24 connected to the pumping chamber 8, a fluidic outlet port 7 leading out of the unit and a reference port 25. This reference port 25 is communicating with the air pressure inside the housing. The valve features an elastic membrane 26 to which the valve body 27 is attached that blocks the outlet port 7. On the inside the membrane 9 is exposed to the pressure of the inlet port 6. On the outside the membrane 9 is exposed to the pressure of the reference port 25. The outlet port's pressure is only present on a negligibly small surface and has thus little influence on the valves behaviour. The valve is designed in such a fashion that the fluid path opens up, only if the inlet port pressure exceeds the reference port pressure by a predefined amount. If the pressure inside the housing increases, the pressure on both inlet and reference port increase likewise and the valve does thus not open.

It should be underlined that the present invention is not limited to the embodiment discussed above. Any other configuration included in the claimed subject-matter is forming part of the invention.

The invention claimed is:

1. A drug infusion pump comprising the following distinct elements:
   a container,
   an outlet channel, and
   a pumping unit;
   said container comprising a rigid wall on which said pumping unit is rigidly fixed;
   said rigid wall further including a passage which forms a direct fluid connection between said pumping unit and said container;
   said outlet channel being directly connected to said pumping unit in such a way that a fluid initially kept in said container may first flow through said pumping unit and then reach said outlet channel;
   said drug infusion pump further comprising an inlet distinct from said outlet channel,
   and wherein the drug infusion pump is made of disposable elements and non-disposable elements, wherein said disposable elements include all elements in contact with the drug, wherein said all elements in contact with the drug comprise the container, the pumping unit, and the inlet.

2. The drug infusion pump according to claim 1 wherein said inlet is adapted to act as refilling means.

3. The drug infusion pump according to claim 1 furthermore comprising a connector and an infusion line that can be connected and disconnected from said outlet channel.

4. The drug infusion pump according to claim 3 wherein said inlet is in close vicinity to the outlet channel and the connector of the infusion line is formed such that it blocks the access to the inlet while connected.

5. The drug infusion pump according to claim 1 characterized by the fact that it is designed to have a pre-determined usage period which is not longer than the labeled life time of use of a drug present in said container.

6. The drug infusion pump according to claim 5 comprising usage preventing means which are adapted to prevent the usage of the device after said pre-determined usage period.

7. The drug infusion pump according to claim 1 wherein the non-disposable elements comprise electronic control parts.

8. The drug infusion pump according to claim 7 wherein said electronic control parts are adapted to prevent usage of the device after a pre-determined period.

9. The drug infusion pump according to claim 8 wherein said electronic control parts are adapted to recognize the identity of the disposable parts in order to prevent reuse after said pre-determined period.

10. The drug infusion pump according to claim 8 wherein said electronic control parts are adapted to determine if said disposable parts have been used previously.

11. The drug infusion pump according to claim 1 furthermore comprising a pressure sensor.

12. The drug infusion pump according to claim 11 wherein said pressure sensor is adapted to measure the liquid pressure inside said container.

13. The drug infusion pump according to claim 12 comprising display means which are adapted to communicate the container filling level to user, said filling level being obtained from said pressure sensor.

14. The drug infusion pump according to claim 12 comprising first alarm means to alert a user in case of excessive filling, said first alarm means being connected to said pressure sensor.

15. The drug infusion pump according to claim 12 comprising second alarm means for detecting potentially dangerous states of reservoir pressure, said second alarm means being connected to said pressure sensor.

16. The drug infusion pump according to claim 12 comprising third alarm means for detecting when the container is empty, said third alarm means being connected to said pressure sensor.

17. The drug infusion pump according to claim 1 wherein said container has a variable volume.

18. The drug infusion pump according to claim 17 wherein said container comprises a movable wall, for instance a flexible wall.

19. The drug infusion pump according to claim 17 comprising a control element that prevents injection into a user when the container is pressurized.

20. The drug infusion pump according to claim 19 wherein said control element is a three ports valve connected to said pumping unit, to said outlet and communicating with said container.

21. The drug infusion pump according to claim 20 wherein said three ports valve is adapted to open only when the pressure on the port connected on the pumping unit is higher than the pressure in or around the container.

22. The drug infusion pump according to claim 17 wherein said container is fabricated as a rigid shell having a concave surface forming a cavity and a flexible membrane covering the cavity.

23. The drug infusion pump according to claim 22 wherein said rigid shell comprises a channel that connects the interior of said container with the external environment.

24. The drug infusion pump according to claim 22 wherein said rigid shell comprises several channels.

25. The drug infusion pump according to claim 22 wherein said flexible membrane is formed to conform to the cavity to allow the container to be emptied without substantial under pressure.

26. The drug infusion pump according to claim 22 comprising an inlet wherein said inlet and said outlet are disposed in said rigid shell.

27. The drug infusion pump according to claim 22 wherein the shape of the cavity in the covering shell is the mirror image of the cavity in the container such that the membrane also conforms to the cover shell in the full state.

28. The drug infusion pump according to claim 22 wherein said flexible membrane is covered with a concave cover shell.

29. The drug infusion pump according to claim 28 adapted in a way so that the volume between the flexible membrane and the cover shell is ventilated for pressure equilibration when the container volume varies.

30. The drug infusion pump according to claim 28 wherein the cover shell is reinforced to protect said flexible membrane from mechanical pressures.

31. The drug infusion pump according to claim 30 wherein said flexible membrane contains a weak zone that breaks in case of dangerous over pressures.

32. The drug infusion pump according to claim 28 wherein said concave cover shell is rigid and thereby limits the container filling volume.

33. The drug infusion pump according to claim 32 comprising limiting means situated between said flexible membrane and said cover shell for reducing the filling volume.

34. The drug infusion pump according to claim 33 wherein the position of said limiting means is adjustable in order to vary the volume reduction.

\* \* \* \* \*